US011273123B2

(12) United States Patent
Dixit et al.

(10) Patent No.: US 11,273,123 B2
(45) Date of Patent: Mar. 15, 2022

(54) CHEWABLE PHARMACEUTICAL DOSAGE FORMS

(71) Applicant: USpharma Ltd, Miami Lakes, FL (US)

(72) Inventors: Manesh A Dixit, Miami Lakes, FL (US); Rahul Botkar, Maharashtra (IN); Partha S Sen, Valsad (IN)

(73) Assignee: USPHARMA LTD, Miami Lakes, FL (US)

( * ) Notice: Subject to any disclaimer, the term of this patent is extended or adjusted under 35 U.S.C. 154(b) by 0 days.

(21) Appl. No.: 16/515,982

(22) Filed: Jul. 18, 2019

(65) Prior Publication Data

US 2020/0022909 A1 Jan. 23, 2020

Related U.S. Application Data

(60) Provisional application No. 62/831,500, filed on Apr. 9, 2019, provisional application No. 62/700,149, filed on Jul. 18, 2018.

(51) Int. Cl.
| | | |
|---|---|---|
| A61K 9/00 | (2006.01) | |
| A61K 31/138 | (2006.01) | |
| A61K 31/167 | (2006.01) | |
| A61K 47/36 | (2006.01) | |

(52) U.S. Cl.
CPC .......... *A61K 9/0056* (2013.01); *A61K 31/138* (2013.01); *A61K 31/167* (2013.01); *A61K 47/36* (2013.01)

(58) Field of Classification Search
CPC ..... A61K 9/0056; A61K 31/138; A61K 47/36
See application file for complete search history.

(56) References Cited

U.S. PATENT DOCUMENTS

| | | | |
|---|---|---|---|
| 4,894,441 A | 1/1990 | Menicagli | |
| 5,837,272 A | 11/1998 | Fierro, Jr. | |
| 5,928,664 A | 7/1999 | Yang | |
| 8,097,279 B2 | 1/2012 | Hassan | |
| 8,496,977 B2 | 7/2013 | Medasani | |
| 8,541,383 B2 | 9/2013 | Gokaraju | |
| 8,802,164 B2 | 8/2014 | Shimoda | |
| 9,072,677 B2 | 7/2015 | Hassan et al. | |
| 9,167,831 B2 | 10/2015 | Subramanian et al. | |
| 9,616,121 B2 | 4/2017 | Agrawal | |
| 9,757,332 B2 | 9/2017 | Kitanaka et al. | |
| 9,764,032 B2 | 9/2017 | Moshtagh | |
| 9,855,288 B2 | 1/2018 | Sinnott | |
| 9,993,447 B2 | 6/2018 | Alevizache et al. | |
| 2002/0076478 A1* | 6/2002 | Grazela | A23G 3/346 426/660 |
| 2002/0086068 A1 | 7/2002 | Bandyopadhyay | |
| 2003/0044456 A1 | 3/2003 | Ichie | |
| 2004/0028622 A1 | 2/2004 | Gurin | |
| 2006/0228412 A1 | 10/2006 | Clouatre et al. | |
| 2007/0196496 A1* | 8/2007 | Farber | A61K 31/718 424/488 |
| 2007/0269386 A1 | 11/2007 | Steen | |
| 2008/0026038 A1 | 1/2008 | Steele | |
| 2008/0125394 A1 | 5/2008 | Savica | |
| 2008/0286252 A1 | 11/2008 | Sinnott | |
| 2009/0130199 A1 | 5/2009 | Kovacs | |
| 2009/0155189 A1 | 6/2009 | Kovacs | |
| 2010/0203078 A1 | 8/2010 | Gokaraju | |
| 2010/0226904 A1 | 9/2010 | Davis | |
| 2010/0330058 A1 | 12/2010 | Davis | |
| 2011/0044964 A1 | 2/2011 | Davis | |
| 2011/0071119 A1 | 3/2011 | Davis | |
| 2011/0313055 A1 | 12/2011 | Ervin | |
| 2012/0061280 A1 | 3/2012 | Cooperman | |
| 2013/0005740 A1* | 1/2013 | Lowther | A23G 3/0053 514/255.04 |
| 2013/0109671 A1 | 5/2013 | Gedulin et al. | |
| 2013/0338093 A1 | 12/2013 | Gedulin et al. | |
| 2014/0212453 A1 | 7/2014 | Chang | |
| 2014/0308374 A1 | 10/2014 | Goel | |
| 2015/0290128 A1 | 10/2015 | Fernandez | |
| 2015/0306029 A1 | 10/2015 | Fernandez et al. | |
| 2015/0374660 A1 | 12/2015 | Goel | |
| 2016/0015777 A1 | 1/2016 | Traylor | |
| 2016/0067180 A1 | 3/2016 | Westhusing et al. | |

(Continued)

FOREIGN PATENT DOCUMENTS

| | | | | |
|---|---|---|---|---|
| WO | WO-9820860 A2 * | 5/1998 | .......... | A61K 9/0056 |
| WO | WO2010101588 A1 | 9/2010 | | |

(Continued)

OTHER PUBLICATIONS

Google Patent Search_Apr. 18, 2020_diphenhydramine + gummy (Year: 2020).*
Google Scholar Search_Apr. 20, 2020_cyclodextrin acetaminophen bitter (Year: 2020).*
Google Scholar Search_Apr. 20, 2020_cyclodextrin bitter blocker drugs (Year: 2020).*
Google Scholar Search_Apr. 20, 2020_hydroxypropyl beta-cyclodextrin acetaminophen bitter (Year: 2020).*
Definition of 'tendency' from Cambridge online dictionary_Apr. 20, 2020 (Year: 2020).*
Danielle R. Reed, Toshiko Tanaka, Amanda H. McDaniel. Diverse tastes: Genetics of sweet and bitter perception. Physiology & Behavior 88 (2006) 215-226. (Year: 2006).*
V. Weiszfeiler, J. Szejtli. "Bitterness Reduction with Beta-Cyclodextrin," Proceedings of the Fourth International Symposium on Cyclodextrins. Advances in Inclusion Science, vol. 5, 1988, pp. 359-366. (Year: 1988).*

(Continued)

*Primary Examiner* — Michael P Cohen
(74) *Attorney, Agent, or Firm* — West Law Office LLC (57) ABSTRACT

One aspect of the present invention concerns compositions and methods of manufacturing translucent chewable gels that are pharmaceutically suitable for oral administration. The chewable gels includes an active pharmaceutical ingredient and a complexing agent. The active pharmaceutical ingredient has a bitter taste. The active pharmaceutical ingredient and the complexing agent are complexed in the form of an inclusion complex. The chewable gels are substantially devoid of bitter taste and/or a tendency to cause oral numbness when chewed.

9 Claims, 5 Drawing Sheets

(56) References Cited

U.S. PATENT DOCUMENTS

| | | |
|---|---|---|
| 2016/0067340 A1 | 3/2016 | Westhusing et al. |
| 2016/0089363 A1 | 3/2016 | Borody |
| 2016/0151279 A1 | 6/2016 | Westhusing et al. |
| 2016/0296470 A1 | 10/2016 | Romanoschi et al. |
| 2016/0310518 A1 | 10/2016 | Gedulin et al. |
| 2017/0157042 A1 | 6/2017 | Fernandez et al. |
| 2017/0173067 A1 | 6/2017 | Sinnott |
| 2017/0209369 A1 | 7/2017 | Westhusing et al. |
| 2017/0209370 A1 | 7/2017 | Westhusing et al. |
| 2017/0251692 A1* | 9/2017 | Yaranossian .......... A23L 29/256 |
| 2017/0274071 A1 | 9/2017 | Agrawal |
| 2017/0368085 A1 | 12/2017 | Gedulin et al. |
| 2018/0071268 A1 | 3/2018 | Borody |
| 2018/0168182 A1 | 6/2018 | Majeed |
| 2018/0177804 A1 | 6/2018 | Papas |

FOREIGN PATENT DOCUMENTS

| | | |
|---|---|---|
| WO | WO2010151275 A1 | 12/2010 |
| WO | WO2011028314 A1 | 3/2011 |
| WO | WO2011034644 A1 | 3/2011 |
| WO | WO2016164470 A1 | 10/2016 |
| WO | WO2018027081 A1 | 2/2018 |
| WO | WO2018236990 A1 | 12/2018 |
| WO | WO2018237000 A1 | 12/2018 |

OTHER PUBLICATIONS

N. Ono, et al. "Reduction of Bitterness of Antihistaminic Drugs by Complexation with β-Cyclodextrins," J. Pharm. Sci. 100: 1935-1943, 2011. (Year: 2011).*

Jane E. Henney, Christine L. Taylor, and Caitlin S. Boon, Editors. Chapter 4, "Strategies to Reduce Sodium Intake in the United States," Washington, D.C.: The National Academies Press, 2010, pp. 91-92. (Year: 2010).*

Google Scholar Search Jan. 25, 2021 (Year: 2021).*

Hydrocolloids Primer, downloaded Jul. 9, 2021 from https://cookingissues.com/primers/hydrocolloids-primer/ Jul. 9, 2021; available on the Web Jul. 6, 2009. (Year: 2009).*

Google Search_Jul. 9, 2021_transpararent gummies carrageenan (Year: 2021).*

Google Patent Search_Jun. 28, 2021_making translucent gummies with carrageenan (Year: 2021).*

European Paediatric Formulation Initiative The 3rd Annual Conference of the EuPFI—Abstracts For Oral Presentations—Topic: Age appropriateness of Formulations—Development and Analysis of Medicated Soft Chew Dosage Form Suitable For Paediatric Use p. 14—2nd Column Sep. 2010; Berlin, Germany.

* cited by examiner

CHEWABLE PHARMACEUTICAL DOSAGE FORMS

RELATED APPLICATIONS

The present application claims the benefit of U.S. Provisional Patent Application Ser. No. 62/700,149, filed Jul. 18, 2018, Chewable Pharmaceutical Dosage Forms and U.S. Provisional Patent Application Ser. No. 62/831,500, filed Apr. 9, 2019, entitled Chewable Pharmaceutical Dosage Forms, each of which is hereby incorporated in its entirety by reference herein.

BACKGROUND

1. Field

The present invention relates generally to pharmaceutical products for human and animal use. More particularly, the present invention relates to orally consumable pharmaceutical products and methods of manufacturing the same. Even more particularly, the present invention relates to chewable pharmaceutical oral dosage forms, including chewable gels. As defined by the United States Pharmacopeia: "[c]hewable gels are used to deliver drug substances and dietary supplements via the oral route. Chewable gels can consist of all or some of the following components—gelling agent(s), sugars, water, sweeteners, and flavoring agents. The sweeteners and flavoring are intended to enhance patient acceptance and mask the taste of the delivered labeled drug substance. Chewable gels maintain their molded shape, are elastic, and yield to mastication. They are intended to be chewed before swallowing. Chewable gels are also known as "gummies" in the confectionary and dietary supplement industries but that term is not used in official article titles" (GC<1151>).

2. Discussion of Prior Art

Chewable oral dosage forms can be an effective way to administer drugs to those who are unable (or unwilling) to swallow traditional oral dosage forms. Known chewable dosage forms tend to lack certain organoleptic properties and are perceived by many patients as being dry, gritty, dusty, and/or bad tasting. Chewable gels could be a suitable alternative; however, chewable gels known in the art are difficult to manufacture (especially on a large scale) and/or suffer from an inability to consistently satisfy generally accepted regulatory standards. Further, many active pharmaceutical ingredients have tastes that are strongly disagreeable, something which manufactures of known chewable gels have failed to overcome. Thus, there is a need for pleasant tasting chewable gels that: include active pharmaceutical ingredients; are capable of commercially viable manufacture; and consistently satisfy generally accepted regulatory standards.

SUMMARY OF THE INVENTION

The following brief summary is provided to indicate the nature of the subject matter disclosed herein. While certain aspects of the present invention are described below, the summary is not intended to limit the scope of the present invention.

One aspect of the present invention concerns chewable gels that can both be manufactured using commercially viable methods (e.g., in commercial batch sizes, etc.) and satisfy generally accepted regulatory standards (e.g., are pharmaceutically suitable) for chewable oral dosage forms.

One aspect of the present invention concerns compositions and methods of manufacturing a translucent chewable gel that is pharmaceutically suitable for oral administration. The chewable gel includes a water insoluble active pharmaceutical ingredient and a complexing agent. The water insoluble active pharmaceutical ingredient has a bitter taste. The water insoluble active pharmaceutical ingredient and the complexing agent are complexed in the form of an inclusion complex. The chewable gel is substantially devoid of bitter taste when chewed.

One aspect of the present invention concerns compositions and methods of manufacturing a translucent chewable gel that is pharmaceutically suitable for oral administration. The chewable gel includes a water soluble active pharmaceutical ingredient and a complexing agent. The water soluble active pharmaceutical ingredient has a bitter taste and a tendency to cause oral numbness. The water soluble active pharmaceutical ingredient and the complexing agent are complexed in the form of an inclusion complex. The chewable gel is substantially devoid of bitter taste and tendency to cause oral numbness when chewed.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached figures, wherein.

The figures do not limit the present invention to the specific embodiments disclosed and described herein. The emphasis instead being placed upon clearly illustrating certain principles of the present invention.

DETAILED DESCRIPTION OF THE PREFERRED EMBODIMENTS

The present invention is susceptible of embodiment in many different forms. While the figures illustrate, and the specification describes, certain preferred embodiments of the invention, it is to be understood that such disclosure is by way of example only. There is no intent to limit the principles of the present invention to the particular disclosed embodiments.

In certain embodiments of the present invention, the composition of the gummy pharmaceutical dosage form (i.e., chewable gel) may include one or more the following components: functional ingredients; active ingredients; complexing agents; co-solvents; gelling agents; non-crystallizing polyol solutions; recrystallization inhibitors; lubricants (release agents); flavors; taste enhancing agents; and/or other additives.

In certain embodiments of the present invention, the composition of the gummy pharmaceutical dosage form has an active ingredient content ranging from about one-tenth of one percent-by-weight (0.1% w/w) to about ten percent-by-weight (10% w/w). As used herein, the phrase "percent-by-weight" (% w/w) refers to the amount/concentration of one or more components in a group of components. The percent-by-weight (% w/w) of one or more components in a group of components can be calculated by dividing the numerical value for the weight of one or more components in a group of components by the numerical value for the weight of all of the components in the group and multiplying the quotient by one-hundred (100).

An active pharmaceutical ingredient (also referred to as active ingredient, pharmaceutically active agent, pharmaceutically acceptable active ingredient, drug, active drug) for use in the process or product according to the current invention is a substance used in a pharmaceutical dosage form, intended to furnish pharmacological activity or to otherwise have direct effect in the diagnosis, cure, mitigation, treatment, and/or prevention of disease. Active ingredients also include compounds that have, or are thought to have, a direct effect in restoring, correcting or modifying physiological functions in a patient population (humans or animals).

As used herein, the phrase "functional ingredient" includes, but is not limited to, minerals, vitamins, nutraceutical agents, and other supplements; including derivatives, salts (and the like), and/or mixtures of the foregoing. A "functional/active" refers to both a functional ingredient and active pharmaceutical ingredient.

Although certain ingredients, such as acetaminophen, diphenhydramine, azithromycin, ibuprofen, dimenhydrinate, amphetamine, fexofenadine, aspirin, dextromethorphan, amoxicillin, cetirizine, and/or methylphenidate, may appear in the examples provided below, it will be understood by those having ordinary skill in the art that other types of active ingredients (and/or functional ingredients) are within the scope of the present invention and that other active ingredients may be used without departing from the spirit of the present invention. For example, the present invention is equally applicable to gummy dosage forms where the active ingredient is selected from a group comprising of anti-inflammatory actives, coronary dilators, cerebral dilators, peripheral vasodilators, anti-infectives, psychotropics, antimanics, stimulants, gastro-intestinal sedatives, antidiarrheal active ingredients, anti-anginal drugs, vasodilators, anti-hypertensive drugs, vasoconstrictors and anti-migraine treatment actives, antibiotics, tranquilizers, antipsychotics, antitumor drugs, anticoagulants and antithrombotic drugs, hypnotics, sedatives, anti-emetics, antinauseants, anticonvulsants, neuromuscular drugs, hyper- and hypoglycemic agents, thyroid and antithyroid preparations, diuretics, antispasmodics, uterine relaxants, nutritional additives, anti-obesity drugs, anabolic drugs, erythropoietic drugs, antiasthmatics, expectorants, cough suppressants, mucolytics, anti-hyperuricemia drugs, antidepressants, and the like, or combinations of the foregoing.

In certain embodiments of the present invention, the gummy dosage form formulation may include drugs used for treatment of Attention Deficit Hyperactivity Disorder (ADHD) selected from a group comprising of methylphenidate, dexmethylphenidate, amphetamine, dextroamphetamine, and lisdexamfetamine dimesylate; including derivatives, salts (and the like), and/or mixtures of the foregoing.

In certain embodiments of the present invention, the gummy dosage form formulation may include *Cannabis* or hemp-based active/functional ingredients including, but not limited to, tetrahydrocannabinol, cannabidiol, and *Cannabis* extracts, derivatives, salts (and the like), and/or mixtures of the foregoing.

In certain embodiments of the present invention, the gummy dosage form formulation includes a complexing agent. A complexing agent is pharmaceutical grade inactive ingredient which forms a complex with functional/active ingredient.

In certain embodiments of the present invention, the composition of the gummy pharmaceutical dosage form has a complexing agent content ranging from about two-tenths of one percent-by-weight (0.2% w/w) to about twenty percent-by-weight (20% w/w).

In certain embodiments of the present invention, cyclodextrins, such as hydroxypropyl-beta cyclodextrin (hereinafter referred to as "HP.beta.CD"), can be used as complexing agents. Cyclodextrins are crystalline, homogeneous, non-hygroscopic substances built-up from glucopyranose units (oligomers of dextrose or its derivatives) joined by α-1,4-linkages. Typical examples include alpha-, beta-, and/or gamma-cyclodextrin; including derivatives and/or mixtures of the foregoing. Cyclodextrins form an active ingredient-cyclodextrin complex (i.e., an inclusion complex), which is an association between the active ingredient and the cyclodextrin and, preferably, takes the form of a clathrate-type inclusion complex, wherein the functional/active ingredient acts as the guest molecule in the enclosed tubular space of the cyclodextrin host, which facilitates increased solubility of functional/active ingredient. It is theorized that this enwrapping of functional/active ingredient (guest) inside cyclodextrin host may prevent interaction of functional/active ingredient with taste buds and/or interact with the gate-keeper proteins of taste buds affecting their functionality resulting in taste masking unpleasant functional/active ingredient.

In certain embodiments of the present invention, it is preferable to maintain a ratio of complexing agent to active ingredient whereby the active ingredient(s) remains substantially complexed with complexing agent (i.e., inclusion complex) to maintain high amounts of water insoluble active ingredient solubilized form, which tends to minimize any disagreeable tastes, such as bitterness, and/or other unpleasant oral sensations, such as numbness of the mouth and tongue, and/or throat irritation that may be associated with the water insoluble (or poorly water soluble) active ingredient. Furthermore, maintaining a ratio of complexing agent to active ingredient whereby active ingredient remains substantially complexed with complexing agent (i.e., inclusion complex) facilitates the formation of a gummy dosage form with superior translucency and enhanced taste. For example, translucent gummy dosage forms that include acetaminophen can be difficult to formulate because acetaminophen has a strong bitter taste and is substantially insoluble in water, which is often a preferred solvent to make gummy dosage forms. When manufacturing such translucent gummy dosage form, it can be imperative to keep all components of the dosage form solubilized, or substantially solubilized, in water. Formation of inclusion complex of acetaminophen and HP.beta.CD in the proper ratio helps to maintain acetaminophen in, or substantially in, solution, which also helps minimize the bitter taste of acetaminophen. In certain embodiments of the present invention, a ratio of complexing agent to active ingredient of at least about one-to-one (1:1) is preferred.

Complexing agents can also facilitate minimization of disagreeable tastes, such as bitterness, and/or other unpleasant oral sensations with water soluble drugs. For example, diphenhydramine hydrochloride, an active ingredient, is known to cause numbness and/or tingling sensations in the mouth when taken via oral route. The inventors hereof found that when gummy dosage forms of the present invention were formulated using, among other ingredients, diphenhydramine hydrochloride complexed with HP.beta.CD in a ratio of complexing agent to active ingredient of about two-to-one (2:1), no numbness or tingling sensation of mouth was perceived upon mastication of the gummy dosage form.

It should be understood that other complexing agents may be used without departing from the spirit of the present invention. Furthermore, as will be understood by those having ordinary skill in the art, certain aspects of the present invention may apply to the use of complexing agents that form different kinds of complexes with functional/active ingredients. Additionally, it should be understood that certain aspects of the present invention are not limited to formulations that include a complexing agent.

In certain embodiments of the present invention, the gummy dosage form formulation includes a buffering agent. A buffering agent is a weak acid or base used to maintain the pH of a dispersion near a desired value during manufacturing process, which, in the context of the present invention, can help minimize molding times (i.e., the amount of time necessary to form a product from the gummy mixture and remove the formed product from the mold) to less that one (1) hour and/or reduce (or in some instances eliminate) the amount of time needed to cure the gummies after they are removed from a forming device.

In certain embodiments of the present invention, trisodium citrate is used in an amount of up to about one percent-by-weight (1% w/w) to maintain the pH of the gummy mixture in the range of about five (5) to about eight (8). It should be understood that other buffering agents may be used without departing from the spirit of the present invention. Furthermore, it should be understood that certain embodiments of the present invention are not limited to formulations that include a buffering agent.

In certain embodiments of the present invention, the gummy dosage form formulation includes a non-acidic antimicrobial agent, such as a tonicity modifying agent. As discussed in greater detail below, the use of tonicity modifying agents reduce the need for acidic antimicrobial agents (e.g., citric acid, fumaric acid, benzoic acid, acetic acid, etc.) to inhibit microbial growth.

In certain embodiments of the present invention, the composition of the gummy pharmaceutical dosage form has a tonicity modifying agent content of less than about two percent-by-weight (2% w/w). In certain embodiments of the present invention, sodium chloride is used as a tonicity modifying agent (and may also facilitate improved taste of gummy dosage forms of the present invention).

It should be understood that other antimicrobial agents may be used without departing from the spirit of the present invention. Additionally, it should be understood that certain embodiments of the present invention are not limited to formulations that include a non-acidic antimicrobial agent.

A gelling agent provides structural integrity to the gummy dosage forms of the present invention. More particularly, gummy dosage forms can be described as a two-phase system consisting of suspended particles in a dispersion medium. The suspended particles (i.e., gelling agents) undergo a high degree of cross-linking or association when hydrated, forming an interlaced three-dimensional structure that provides structural integrity to chewable gel.

In certain embodiments of the present invention, the composition of the gummy pharmaceutical dosage form has a gelling agent content ranging from about one-tenth of one percent-by-weight (0.1% w/w) to about twenty percent-by-weight (20% w/w).

Gelling agents of the present invention may include, but are not limited to, the group comprising of gelatin, alginate, carrageenan, dextran, gellan, guar gum, hyaluronic acid, pullulan, xanthan, xyloglucan, pectins, chitosan, tapioca and the like; including combinations of the foregoing. It should be understood that other gelling agents may be used without departing from the spirit of the present invention.

Carrageenan is a naturally occurring polysaccharide derived from different species of Rhodophyceae (red seaweed). There are three primary families of carrageenan based on the position of sulfate groups and the presence or absence of anhydrogalactose: lambda, iota, and kappa, with iota-carrageenan being preferred in certain embodiments of the present invention. Carrageenan does not exhibit thermoreversible gelling property and is stable in accelerated conditions of temperature (e.g., about thirty-seven degrees Celsius (37° C.) to about forty-three degrees Celsius (43° C.)) and relative humidity (about seventy percent relative humidity (70% RH) to about eighty percent relative humidity (80% RH)) in accordance with guidelines set by the International Council for Harmonisation of Technical Requirements for Pharmaceuticals for Human Use (ICH).

In some embodiments of the present invention, the dosage form contains carrageenan in a concentration of at least one percent-by-weight (1.0% w/w).

Additional information relating to gelling agents can be found in the Handbook of Pharmaceutical Excipients (Raymond C Rowe et al. eds., 6th ed. 2009), which is incorporated herein by reference in its entirety. Additional information concerning carrageenan process can be found in the Handbook of Hydrocolloids (Glyn O. Phillips et al., eds., 2nd ed. 2009), which is incorporated herein by reference in its entirety.

In certain embodiments of the present invention, the gummy dosage form formulation includes a co-solvent. A co-solvent is either a water-miscible or partially miscible organic solvent, that facilitates reduction of strong interactions between water molecules and hence reduces the ability of water to precipitate out non-polar solute. Co-solvents work synergistically with complexing agents like cyclodextrins to increase the solubility of the functional/active ingredient, which, as discussed above, facilitates the formation of a gummy dosage form with improved translucency and taste. The exact mechanism of synergism between co-solvent and cyclodextrins is not clear; however, it is assumed that when a co-solvent is introduced into solution containing the inclusion complex, co-solvents facilitate formation of a drug bearing binary/ternary complex increasing solubility of the functional/active ingredient.

In certain embodiments of the present invention, the composition of the gummy pharmaceutical dosage form has a co-solvent content ranging from about one-half of one percent-by-weight (0.5% w/w) to about fifty percent-by-weight (50% w/w).

In certain embodiments of the present invention, the co-solvent is selected from a group comprising of polyethylene glycol (hereinafter referred to as "PEG"), propylene glycol, glycerin/glycerol, sorbitol, maltitol, and the like; including combinations of the foregoing. However, it should be understood that other co-solvents may be used without departing from the spirit of the present invention.

In certain embodiments of the present invention, the gummy dosage form formulation includes a recrystallization inhibitor. Recrystallization inhibitors aid to inhibit recrystallization of certain ingredients in the composition and can also reduce irritability of functional/active ingredient on oral mucosa, which aids in masking unpleasant taste of active/functional ingredients and mixtures thereof.

Formulations of the present invention may include one or more recrystallization inhibitors selected from group consisting of polyvinyl alcohol (hereinafter referred to as "PVA"), mannitol, sodium carboxymethyl cellulose (hereinafter referred to as "CMCNa"), hydroxypropyl methylcellulose (hereinafter referred to as "HPMC"), and povidone (also known as polyvinylpyrrolidone, and hereinafter referred to as "PVP"), and the like; including combinations of the foregoing. However, it should be understood that other recrystallization inhibitors may be used without departing from the spirit of the present invention.

In certain embodiments of the present invention, the composition of the gummy pharmaceutical dosage form may have a recrystallization inhibitor content ranging from about one-tenth of one percent-by-weight (0.1% w/w) to about five percent-by-weight (5% w/w).

In certain embodiments of the present invention, the gummy dosage form formulation includes a non-crystallizing polyol solution. Non-crystallizing polyol solutions provide a sweet taste and will not, under conditions presented herein, precipitate out of solution. Additionally, non-crystallizing polyol solutions may contribute to an increased solubility of the gummy dosage form formulation; for instance, in formulations containing sugar, non-crystallizing polyol solutions can prevent or reduce recrystallization of solubilized sugar from the gummy composition. If solubilized sugar recrystallizes from the gummy composition, the chewable gels formed therefrom may not have the translucent appearance that is preferred in many embodiments of the present invention.

Formulations of the present invention may also include one or more non-crystallizing polyol solutions selected from group consisting of non-crystallizing sorbitol solution, maltitol solution, and the like; including combinations of the foregoing. Other non-crystallizing polyol solutions may be used without departing from the spirit of the present invention.

In certain embodiments of the present invention, the gummy dosage form formulation includes lubricating agents (also referred to as a release agents). Lubricating agents facilitate formation of the gummy dosage form by preventing the occurrence of damaging contact between the gummy and surfaces of dosage form forming devices. In certain embodiments of the present invention, the gummy dosage form formulation may have a lubricant content ranging from about one-tenth of one percent-by-weight (0.1% w/w) to about five percent-by-weight (5% w/w).

Formulations of the present invention may include at least one lubricating agent selected from group consisting of mineral oil, light mineral oil, and the like; including combinations of the foregoing. Both mineral oil and light mineral oil are transparent, colorless, viscous oily liquids, without fluorescence in daylight. They are practically tasteless and odorless when cold, and have a faint odor when heated. It should be understood that other lubricating agents may be used without departing from the spirit of the present invention. Furthermore, it should be understood that certain embodiments of the present invention are not limited to formulations that include a lubricating agent.

Formulations of the present invention may also include one or more flavor compositions, for example, fruit flavor compositions, botanical flavor compositions, or mixtures thereof. The particular amount of the flavor component useful for imparting flavor characteristics to the composition of the present invention will depend upon the flavor(s) selected, the flavor impression desired, and the form of the flavor component. Those skilled in the art are readily able to determine the amount of any flavor component(s) used to achieve the desired flavor impression. It should be understood that a wide range of favor compositions may be used without departing from the spirit of the present invention. Furthermore, it should be understood that certain embodiments of the present invention are not limited to formulations that include a favor composition.

In certain embodiments of the present invention, the gummy dosage form formulation may include taste enhancing agents. Taste enhancing agents are substances that may enhance or suppress perceived tastes and/or smells. Also, taste enhancing agents may provide a perceived flavor.

In certain embodiments of the present invention, taste enhancing agents may include taste masking powders, bitter blocker powders, and/or sweeting agents such as dextrose, neotame, and sucralose. It should be understood that other taste enhancing agents may be used without departing from the spirit of the present invention.

In certain embodiments of the present invention, the composition of the gummy pharmaceutical dosage form includes coloring agents such as dyes and pigments. It should be understood that a wide range of coloring agents may be used without departing from the spirit of the present invention. Furthermore, it should be understood that certain embodiments of the present invention are not limited to formulations that include a coloring agent.

In some embodiments of the present invention, a single excipient has more than one function in the gummy formulation. In certain embodiments of the present invention glycerol may serve a multi-purpose role as a co-solvent and a humectant. In certain embodiments of the present invention, maltitol solution may serve a multi-purpose role as a co-solvent and recrystallization inhibitor. In certain embodiments of the present invention, caster sugar may serve a multi-purpose role as a sweetener and humectant.

In certain embodiments of the present invention, it may be preferable to maintain a product temperature below about one hundred five degrees Celsius (105° C.). Product temperature generally refers to actual temperature at which product is maintained during different stages of manufacturing. Processing temperature refers to a temperature that enables the product temperature to be maintained during various stages of manufacturing. Known processes of manufacturing gummy dosage forms and/or gummy products require higher product temperatures, which can be problematic and/or impractical for the manufacture of pharmaceutical grade gummy dosage forms. For instance, satisfaction of regulatory requirements for pharmaceuticals including, but not limited to, efficacy and safety, is problematic using known processes because of, among other things, difficulties relating to: controlling the assay of active ingredient; providing a unit dosage form having acceptable content uniformity; and achieving acceptable drug degradation limits. Additionally, known processes of manufacturing gummy dosage forms do not enable addition of the active/function ingredient near the end of the heating process based on the viscosity and dynamic solid content (% w/w) of the heated gummy mixture, which may result in a unit dosage form having unacceptable content uniformity. Furthermore, known processes of manufacturing gummy dosage forms and/or gummy products at higher product temperatures often require that the higher product temperature of the final gummy mixture be maintained, or substantially maintained, until the final gummy mixture is transferred to a mold or other forming device. Moreover, such known processes often require substantial conditioning to a considerably lower temperatures for formation of and/or curing of the final dosage form (i.e., final formed structure), which adds to the duration of processing time (negatively impacting the commercial viability). The foregoing limitations of known processes can be overcome by, among other things, maintaining a constant solid content (% w/w) of the gummy mixture during by proper control of product temperature below about one hundred five degrees Celsius (105° C.) during certain/specific stages of manufacturing.

In certain embodiments of the present invention, it may be preferable to maintain the pH of the gummy mixture in the range of about five (5) to about eight (8). Preferably, the pH of the gummy mixture according to the present invention is maintained in the range of about five (5) to about eight (8) without the use of acid preservatives (e.g., citric acid, fumaric acid, benzoic acid, acetic acid, etc.). Gummies formed by known processes typically have a high-water content (e.g., twenty (20) to thirty-five (35) percent-by-weight), which often requires the addition of acid preservatives to the gummy mixture to prevent microbial spoilage. Characteristically, acid preservatives do not kill microorganisms but inhibit their growth by extending lag phases. Generally, acid preservatives are more effective at low pH values (where solutions contain increased concentrations of undissociated acids), where they become increasingly potent as antimicrobial agents. In gummy formulations that include carrageenan, the use of acid preservatives may be problematic to due to autohydrolysis of carrageenan in gummy mixtures having lower pH levels (and higher temperatures), which can result in, among other things: an increased molding time; and/or a prolonged curing period. In certain embodiments of the present invention, use of a buffering agent (e.g., trisodium citrate) can facilitate a pH of the gummy mixture in a range of about five (5) to about eight (8), which can lead to faster molding times (i.e., less than one (1) hour).

In certain embodiments of the present invention, non-acidic antimicrobial agents, such as tonicity modifying agents, can be used to control microbial content. For instance, sodium chloride can be used to provide a gummy dosage form composition with a relatively high osmotic pressure gradient (hypertonic), which inhibits microbial growth. This inhibition of microbial growth can be corroborated by the low water activity ($a_w$) of the product. Water activity ($a_w$) of a product is the ratio between the vapor pressure of the product itself, when in a completely undisturbed balance with the surrounding air media, and the vapor pressure of distilled water under identical conditions. Water activity ($a_w$) has its most useful application in predicting the growth of bacteria, yeast, and mold. It is well known that for an orally consumable product to have a useful shelf life without relying on refrigerated storage, it is necessary to control either its acidity level (pH) or the level of water activity ($a_w$) or a suitable combination of the two. This can effectively increase the product's stability and make it possible to predict its shelf life under known ambient storage conditions. In certain embodiments of the present invention, the average water content in the unit gummy dosage form is about eighteen percent (18%) to about twenty-two percent (22%), with a water activity ($a_w$) of up to 0.75, which provides, among other things, a unit gummy dosage form having a longer shelf life than what is known in the art.

Solid content is the percentage of solid/dry matter in the formulation. Solid content (SC) can be computed using the following equation: SC=100−((((mass of the wet sample)−(mass of the dry sample))÷(mass of the wet sample))×100). For example, if the mass of the dry sample is thirty grams (30 g) and the mass of the wet sample is forty-five grams (45 g), then the solid content would be approximately sixty-six and seven-tenths percent-by-weight (66.7% w/w). Solid content be measured using various instruments, including refractometer meters. A refractometer is an optical instrument that employs the measurement of refractive index of a composition to determine the solid content of the composition. In certain embodiments of the present invention, it is preferable for the gummy mixture to have a solid content ranging from about seventy (70% w/w) to about eighty percent-by-weight (80% w/w); and more preferably ranging from about seventy-four percent-by-weight (74% w/w) to about eighty percent-by-weight (80% w/w). If the solid content is too high or too low, then the gummy dosage forms (gummies) formed may be too sticky or too brittle, respectively. Gummy dosage forms that are too sticky or too brittle will not have the preferred organoleptic properties of the present invention. Further, gummy dosage forms that are too sticky can be difficult to remove from molds (e.g., sticking to the mold), and dosage forms that are too brittle tend to be easily breakable.

As discussed above, the present invention is not limited to any particular dosage form forming device. Many different devices and methods make be used to facilitate shaping the gummy dosage forms without departing from the spirit of the present invention.

The present invention is not limited to any particular means of transferring the gummy mixture to the dosage form forming device(s). With reference to certain manufacturing processes of the present invention, in some embodiments, the gummy mixture may be transferred to the dosage form forming device(s) by pouring or other means of transfer whereby gravity is the primary motive force inducing flow. With reference to certain manufacturing processes of the present invention, in some embodiments, it is preferable to mechanically induce flow of gummy mixture to facilitate transfer of the mixture to the dosage form forming device(s). For example, a wide range of pumping devices may be used to facilitate transfer of the gummy mixture to the dosage form forming device or other means of transfer whereby gravity is the primary motive force inducing flow are not sufficient. It should be understood by those having ordinary skill in the art that transferring the gummy mixture to the dosage form forming device(s) may be accomplished by many different ways, including the use of many different types of devices, without departing from the spirit of the present invention. Additionally, it should be understood that gummy dosage forms of the present invention may be made using a continuous process including, but not limited to, mogul-type production systems.

With reference to certain manufacturing processes of the present invention, in some embodiments, the gummy mixture is removed from the dosage form forming device after drying. Drying the gummy mixture may be accomplished in several different ways without departing from the spirit of the present invention. For example, in certain embodiments of the present invention, the gummy mixture is allowed to dry in the dosage form forming device at ambient temperature (also referred to as room temperature) for a duration of time ranging from about twenty (20) to about thirty (30) minutes (dry time) before the gummy dosage forms are removed. The dry time may be reduced by adjusting a dry time parameter. For example, in certain embodiments of the present invention, the gummy mixture is dried at a temperature ranging from about two degrees Celsius (2° C.) to about five degrees Celsius (5° C.) for a duration of time ranging from about ten (10) minutes to about fifteen (15) minutes before the gummy dosage forms are removed. Different/additional drying parameters (e.g., temperature, etc.) may be used without departing from the spirit of the present invention. As will be discussed in greater detail below, in certain embodiments of the present invention, the gummy dosage forms are cured after being removed from dosage form forming device. In certain embodiments of the present invention, the gummy dosage forms are cured within the dosage form forming device.

The means of removing the dosage forms from the dosage form forming device may vary depending on the type of dosage form forming device being used. It should be understood by those having ordinary skill in the art that many different types of dosage form forming device may be used without departing from the spirit of the present invention.

Preferably, once the gummy mixture has sufficiently dried in the dosage form forming device, the individual gummy dosage forms of the present invention are removed. Undesired defects to the appearance and/or shape of the individual chewable/gummy dosage forms of the present invention may occur if improperly removed. Those having ordinary skill the art will appreciate that such defects can increase manufacturing costs.

With reference to certain manufacturing processes of the present invention, in some embodiments, the gummy dosage forms are cured after removal from the dosage form forming device. Curing period parameters (e.g., duration, temperature, etc.) are important for producing a gummy dosage form that is physically stable. For example, a curing period that is too long may result in dosage forms that are too hard. Conversely, if the curing period is too short, the resulting dosage forms may be sticky, misshapen, and/or easily deformed. In certain embodiments of the present invention, the gummy dosage forms are cured at room temperature for a duration of about forty-eight hours (cure period). Curing methods having different/additional parameters (e.g., temperature, etc.) may be used without departing from the spirit of the present invention. As discussed above, in certain embodiments of the present invention, the gummy dosage forms may be cured without first being removed from the dosage form forming device.

Examples: the following Examples set forth preferred therapeutic agents and methods in accordance with the invention, but it is to be understood that these examples are given by way of illustration only, and nothing therein should be taken as a limitation upon the overall scope of the invention.

Example 1: ingredients corresponding to Example 1 are tabulated in Table 1, with the amount of each ingredient given in respective percent-by-weight (% w/w).

TABLE 1

| Ingredient Name | Quantity (% w/w) |
| --- | --- |
| Acetaminophen | 2.86 |
| FD&C Red 40 | 0.1 |
| HP.beta.CD | 8.54 |
| Glycerin | 4.11 |
| PEG 400 | 1.23 |
| Strawberry Flavor | 0.49 |
| Gelatin | 13.55 |
| Light Mineral Oil | 0.18 |
| Citric acid | 0.8 |
| Maltitol solution | 47.96 |
| PVA | 0.49 |
| PVP K30 | 0.49 |
| Dextrose | 1.04 |
| Sucralose | 0.56 |
| Purified Water | 17.58 |
| TOTAL | 100 |

Procedure—Example 1

STEP I: add about half the quantity of purified water into a container and heat to about sixty-five degrees Celsius (65° C.), then add and dissolve the quantities of acetaminophen and HP.beta.CD under stirring, until clear solution is observed.

STEP II: add the remaining quantity of purified water to a separate container and heat to about eighty-five degrees Celsius (85° C.), then add and dissolve the quantities of PVA and PVP K30 under stirring, until clear solution is observed.

STEP III: combine the mixtures from STEP II and STEP I under continuous stirring. Add and disperse the quantity of gelatin under continuous stirring for at least about ten (10) minutes, maintain temperature at about eighty-five degrees Celsius (85° C.).

STEP IV: add and mix the quantity of maltitol solution into contents of STEP III. Add and dissolve quantities of dextrose and sucralose with continuous stirring.

STEP V: combine and mix the batch quantities of glycerin, mineral oil, PEG 400, strawberry flavor, and FD&C Red 40 in a separate container.

STEP VI: combine the mixture of STEP V and the mixture of STEP IV. Add and dissolve the quantity of citric acid under continuous stirring until a homogenous solution obtained.

STEP VII: transfer the gummy mixture from STEP VI to a product mold, allow the gummy mixture to stand for about fifteen (15) to about forty-five (45) minutes before removing the gummy dosage forms from the mold.

Example 2: ingredients corresponding to Example 2 are tabulated in Table 2, with the amount of each ingredient given in respective percent-by-weight (% w/w).

TABLE 2

| Ingredient Name | Quantity (% w/w) |
| --- | --- |
| Diphenhydramine Hydrochloride | 0.52 |
| FD&C Red 40 | 0.1 |
| HP.beta.CD | 10 |
| Glycerin | 4.11 |
| PEG 400 | 1.23 |
| Strawberry Flavor | 0.49 |
| Gelatin | 12.5 |
| Mineral Oil | 0.18 |
| Citric acid | 0.8 |
| Maltitol solution | 49.98 |
| PVA | 0.49 |

TABLE 2-continued

| Ingredient Name | Quantity (% w/w) |
|---|---|
| PVP K-30 | 0.49 |
| Dextrose | 1.04 |
| Sucralose | 0.56 |
| Purified Water | 17.57 |
| TOTAL | 100 |

Procedure—Example 2

STEP I: add about half of the quantity of purified water to a container and heat to about sixty-five degrees Celsius (65° C.). Add the quantities of diphenhydramine hydrochloride and HP.beta.CD to the purified water under stirring until clear solution is observed.

STEP II: add the remaining batch quantity of purified water into a separate container and heat to about eighty-five degrees Celsius (85° C.). Add and disperse the batch quantities of PVA and PVP K-30 under stirring to until clear solution is observed.

STEP III: combine the contents of STEP II and STEP I under continuous stirring. Add and disperse the batch quantity of gelatin under continuous stirring for approximately ten (10) minutes, maintaining temperature at about eighty-five degrees Celsius (85° C.).

STEP IV: add and mix the batch quantity of maltitol solution into contents of STEP III. Add and dissolve the batch quantities of dextrose and sucralose with continuous stirring.

STEP V: combine and mix batch quantities of glycerin, mineral oil, PEG 400, strawberry flavor, and FD&C Red 40 in a separate container.

STEP VI: combine contents from STEP V and STEP IV. Add and dissolve the batch quantity of citric acid under continuous stirring until a homogenous solution obtained.

STEP VII: transfer the gummy mixture from STEP VI to a product mold, cool to room temperature, and remove the gummy from the mold after cooling for about thirty to forty-five (30-45) minutes.

Example 3: ingredients corresponding to Example 3 are tabulated in Table 3, with the batch quantity amount of each ingredient given grams (g).

TABLE 3

| Ingredient Name | Ingredient Type | Batch Quantity (g) |
|---|---|---|
| Diphenhydramine hydrochloride | active ingredient | 514.8 |
| Sodium chloride | tonicity modifying agent | 330 |
| Trisodium citrate | buffering agent | 264 |
| Bubble gum flavor | flavor | 33 |
| Carrageenan | gelling agent | 1650 |
| HP.beta.CD | complexing agent | 1273 |
| Maltitol solution | non-crystallizing polyol solution | 5544 |
| Bitter blocker powder | taste enhancing agent | 238 |
| Corn syrup | taste enhancing agent/filler | 26730 |
| Neotame | taste enhancing agent | 33 |
| Sucralose | taste enhancing agent | 330 |
| Sugar | taste enhancing agent/filler | 15840 |
| Purified water | water | 23100 |
| TOTAL | | 75880 |

Procedure—Example 3

A twelve and one-half milligram (12.5 mg) diphenhydramine hydrochloride translucent gummy pharmaceutical dosage form composition and procedure:

STEP I: add about two thousand grams (2000 g) of purified water to a container. Slowly add the batch quantity of HP.beta.CD to the purified water under continuous stirring for approximately thirty (30) minutes.

STEP II: add the batch quantity of diphenhydramine hydrochloride to the mixture of STEP I under continuous stirring, a clear solution should be observed after approximately fifteen (15) minutes.

STEP III: add about twenty thousand five hundred grams (20500 g) of purified water to a container. Slowly add the batch quantities of sodium chloride, bitter blocker powder, sucralose, and neotame under stirring for approximately fifteen (15) minutes until clear solution observed.

STEP IV: add the batch quantity of corn syrup to the solution of STEP III under stirring for approximately ten (10) minutes and heat to a temperature in the range of about fifty degrees Celsius (50° C.) to about fifty-five degrees Celsius (55° C.).

STEP V: create a dry mix blend by combining the batch quantity of carrageenan, the batch quantity of trisodium citrate, and about two thousand grams (2000 g) sugar and mix for approximately ten (10) minutes.

STEP VI: add the dry mix blend from STEP V to the heated mixture of STEP IV under stirring and heat the mixture a temperature in the range of about fifty degrees Celsius (50° C.) to about fifty-five degrees Celsius (55° C.) under constant stirring.

STEP VII: heat the gummy mixture from STEP VI to about ninety a temperature in the range of about ninety degrees Celsius (90° C.) to about one hundred five degrees Celsius (105° C.), add the batch quantity of maltitol solution and the remaining batch quantity of sugar, and continue heating the mixture to a temperature in the range of about ninety degrees Celsius (90° C.) to about one hundred five degrees Celsius (105° C.) for approximately ninety (90) minutes until the total solid content raises to about seventy-four percent-by-weight (74% w/w) or about seventy-four brix (74 Brix).

STEP VIII: combine the solution of STEP II and the mixture of STEP VII under stirring and maintain a temperature in the range of about ninety degrees Celsius (90° C.) to about one hundred five degrees Celsius (105° C.) until total solid content raises to about seventy-four percent-by-weight (74% w/w) or about seventy-four brix (74 Brix).

STEP IX: add and dissolve the batch quantity of bubble gum flavor to the remaining batch quantity of purified water to a container.

STEP X: combine the solution of STEP IX to mixture of STEP VIII under stirring and maintain a temperature in the range of about ninety-five degrees Celsius (95° C.) to about one hundred five degrees Celsius (105° C.).

STEP XI: transfer the gummy mixture from STEP X to a product mold, cool to room temperature, and remove the gummy from the mold after cooling for about ten (10) to about fifteen (15) minutes.

EXAMPLE 4: Ingredients corresponding to Example 4 are tabulated in Table 4, with the batch quantity amount of each ingredient given grams (g).

TABLE 4

| Ingredient Name | Batch Quantity (g) |
| --- | --- |
| Diphenhydramine hydrochloride | 468 |
| Sodium chloride | 300 |
| Trisodium citrate | 240 |
| Pink color | 60 |
| Bubble gum flavor | 60 |
| Carrageenan | 1500 |
| Maltitol solution | 5040 |
| Bitter blocker | 216 |
| Corn syrup | 24300 |
| Neotame | 30 |
| Sucralose | 300 |
| Sugar | 15220 |
| Purified water | 21000 |
| TOTAL | 68734 |

Procedure—Example 4: a twelve and one-half milligram (12.5 mg) diphenhydramine hydrochloride translucent chewable pharmaceutical dosage form composition and procedure:

STEP I: add nineteen thousand and five-hundred grams (19,500 g) of purified water to a container. Slowly add the batch quantities of sodium chloride, bitter blocker powder, sucralose, and neotame under stirring for approximately fifteen (15) minutes until clear solution observed.

STEP II: add the batch quantity corn syrup to the solution of STEP I under stirring for approximately ten (10) minutes and heat to a temperature in the range of about fifty degrees Celsius (50° C.) to about fifty-five degrees Celsius (55° C.).

STEP III: prepare a dry mix blend by combining the batch quantity of carrageenan, the batch quantity of trisodium citrate, and two thousand grams (2000 g) of sugar and mix for approximately ten (10) minutes.

STEP IV: add the dry mix blend from STEP III to the heated solution of STEP II under stirring.

STEP V: heat the gummy mixture from STEP IV, while stirring, to a temperature in the range of about ninety degrees Celsius (90° C.) to about one hundred five degrees Celsius (105° C.).

STEP VI: add the batch quantity of maltitol solution and fifteen thousand two hundred twenty (15,220 g) of sugar to the gummy mixture of STEP V under stirring; and continue heating the gummy mixture to a temperature in the range of about ninety degrees Celsius (90° C.) to about one hundred five degrees Celsius (105° C.) until total solid content raises to about seventy-four percent-by-weight (74% w/w) or about seventy-four brix (74 Brix).

STEP VII: in a container, add and dissolve the batch quantities of diphenhydramine hydrochloride, bubble gum flavor, and pink color in about one thousand five hundred (1500 grams) of purified water.

STEP VIII: combine the mixtures of STEP VI to mixture of STEP VII under stirring and maintain a temperature in the range of about ninety-five degrees Celsius (95° C.) to about one hundred five degrees Celsius (105° C.).

STEP IX: transfer the gummy mixture from STEP VIII to a product mold, cool to room temperature, and remove the gummy from the mold after cooling for about for about ten (10) to about fifteen (15) minutes.

Example 5: ingredients corresponding to Example 5 are tabulated in Table 5, with the amount of each ingredient given in respective percent-by-weight (% w/w).

TABLE 5

| Ingredient Name | Batch Quantity (g) |
| --- | --- |
| Acetaminophen | 15.00 |
| Sodium chloride | 1.50 |
| Trisodium citrate | 1.20 |
| FD&C Yellow | 0.30 |
| HP.beta.CD | 37.50 |
| Pineapple flavor | 1.50 |
| Carrageenan | 7.50 |
| Maltitol solution | 12.87 |
| Bitter blocker | 1.08 |
| Corn syrup | 121.50 |
| Neotame | 0.15 |
| Sucralose | 1.50 |
| Sugar | 38.17 |
| Purified water | 105.00 |
| TOTAL | 344.77 |

Procedure—Example 5

STEP I: add purified water to a container; add the batch quantities of HP.beta.CD and acetaminophen under stirring for approximately fifteen (15) minutes.

STEP II: heat the mixture from STEP I to a temperature in the range of about fifty degrees Celsius (50° C.) to about fifty-five degrees Celsius (55° C.) while stirring; clear solution observed after approximately fifteen (15) minutes;

STEP III: add purified water to a container; add the batch quantities of sodium chloride, sucralose, neotame, and bitter blocker under stirring; clear solution observed after approximately fifteen (15) minutes;

STEP IV: add the batch quantity of corn syrup to the solution of STEP III under stirring; heat a temperature in the range of about fifty degrees Celsius (50° C.) to about fifty-five degrees Celsius (55° C.) while stirring; clear solution observed.

STEP V: prepare a dry mix blend by combining the batch quantity of carrageenan, the batch quantity of trisodium citrate, and 10 grams (10 g) of sugar and mix for approximately ten (10) minutes.

STEP VI: add the dry mix blend from STEP V to the heated solution of STEP IV under constant stirring for approximately twenty (20) minutes;

STEP VII: heat the gummy mixture from STEP VI to a temperature in the range of about ninety degrees Celsius (90° C.) to about ninety-five degrees Celsius (95° C.); add the batch quantity of maltitol solution and the remaining batch quantity of sugar; heat the gummy mixture to and maintain a temperature in the range of about one hundred degrees Celsius (100° C.) to about one hundred five degrees Celsius (105° C.) for approximately ninety (90) minutes until the total solid content raises to seventy-four percent (74% w/w) or about seventy-four brix (74 Brix)

STEP VIII: combine the solution of STEP II and the gummy mixture of STEP VII under stirring; maintain a temperature in the range of about ninety-five degrees Celsius (95° C.) to about one hundred five degrees Celsius (105° C.) until the total solid content is about seventy-four percent-by-weight (74% w/w) or about seventy-four brix (74 Brix).

STEP IX: transfer the gummy mixture from STEP VIII to a product mold, cool to room temperature, and remove the gummy from the mold after cooling for about fifteen (15) to twenty (20) minutes.

Unlike known gummy dosage forms (and processes of manufacturing gummy dosage forms and/or gummy products), gummy dosage forms of the present invention are able to satisfy generally accepted regulatory standards for chewable oral dosage forms, including, assay, content uniformity, disintegration time, dissolution, impurity (degradation) content, stability, and translucency.

One preferred method of measuring the content uniformity of gummy dosage forms of the present invention is the Harmonized standard for Uniformity of Dosage Units as adopted by the United States Pharmacopeial Convention (<905> Uniformity of Dosage Units).

One preferred method of measuring the disintegration of gummy dosage forms of the present invention is the disintegration test procedure as adopted by the United States Pharmacopeial Convention (general chapter <701>). Preferably, gummy dosage forms of the present invention have a disintegration rate will disintegrate in less than about sixty (60) minutes when analyzed in accordance with this test.

Values for the disintegration time, water content, and average assay corresponding to MGP 1 and the dosage forms formed in accordance with Examples 1 and 2 are compiled in Table 6.

TABLE 6

| Sample | Disintegration Time (Mins.) | Water Content (% w/w) | Average Assay (%) |
|---|---|---|---|
| MGP 1 | 16 | — | — |
| EX 1 | 22 | — | 101 |
| EX 1[1] | — | — | 101 |
| EX 1[2] | | | 104 |
| EX 2 | 20 | 6.4 | 104 |

Footnote
[1]Example 1 (1 Month Stability) (30° C./75% RH)
[2]Example 1 (3 Month Stability) (25° C./60% RH).

Figure 1:
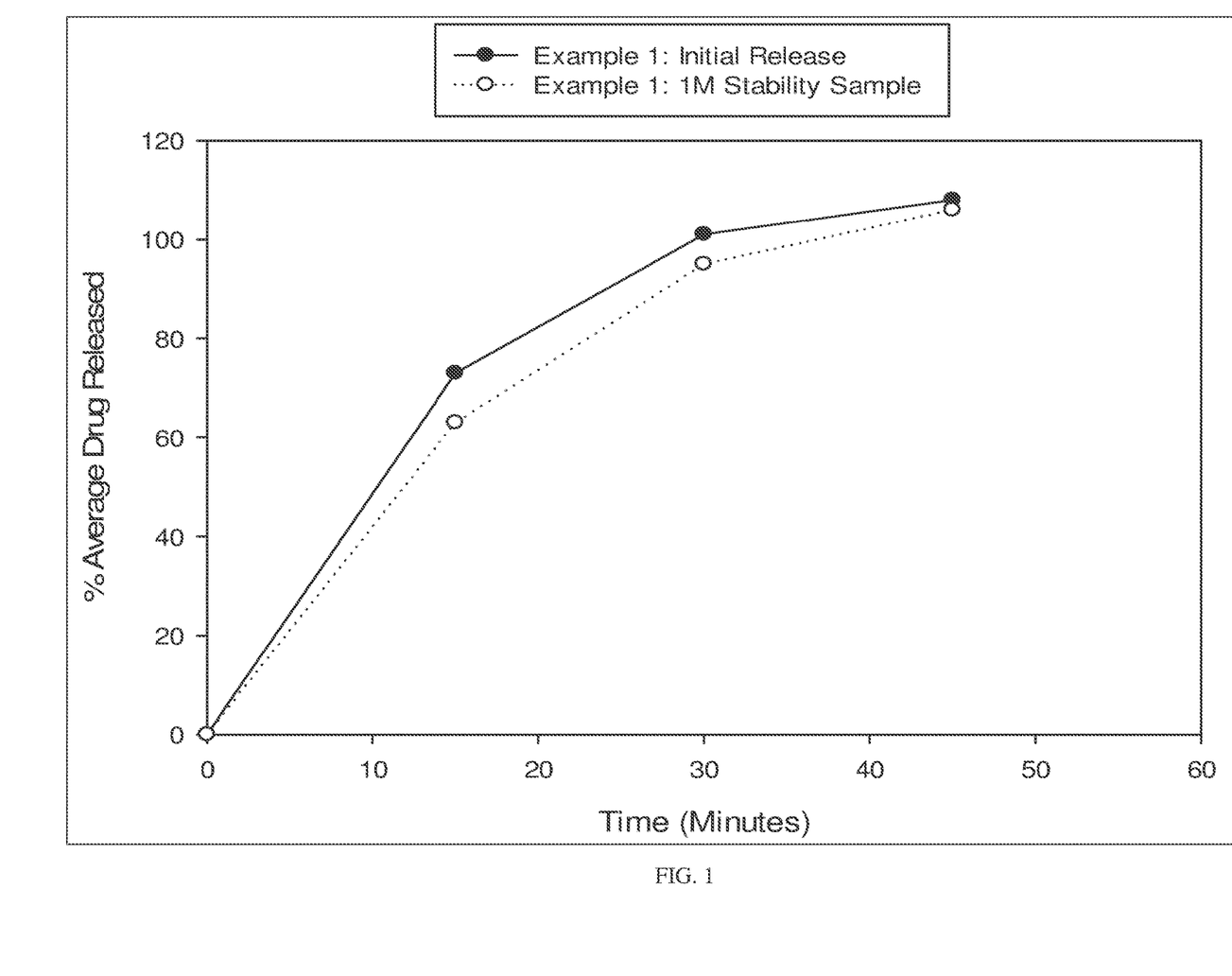
FIG. 1 is a chart showing the dissolution profiles (dissolution vs. time) of gummy dosage forms formed in accordance with Example 1 (initial release and stability sample)

FIG. 1 shows the plot of the dissolution vs. time of gummy dosage forms formed in accordance with Example 1 (initial release and one month stability sample). Dissolution profile analysis was performed in water medium, using United States Pharmacopeia-apparatus II (Paddle Apparatus), nine hundred milliliters (900 ml), seventy-five rotations per minute (75 rpm). The stability sample for gummy dosage form formed in accordance with Example 1 was stored for one-month at thirty degrees Celsius (30° C.) and seventy-five percent (75%) relative humidity (RH).

Figure 5:
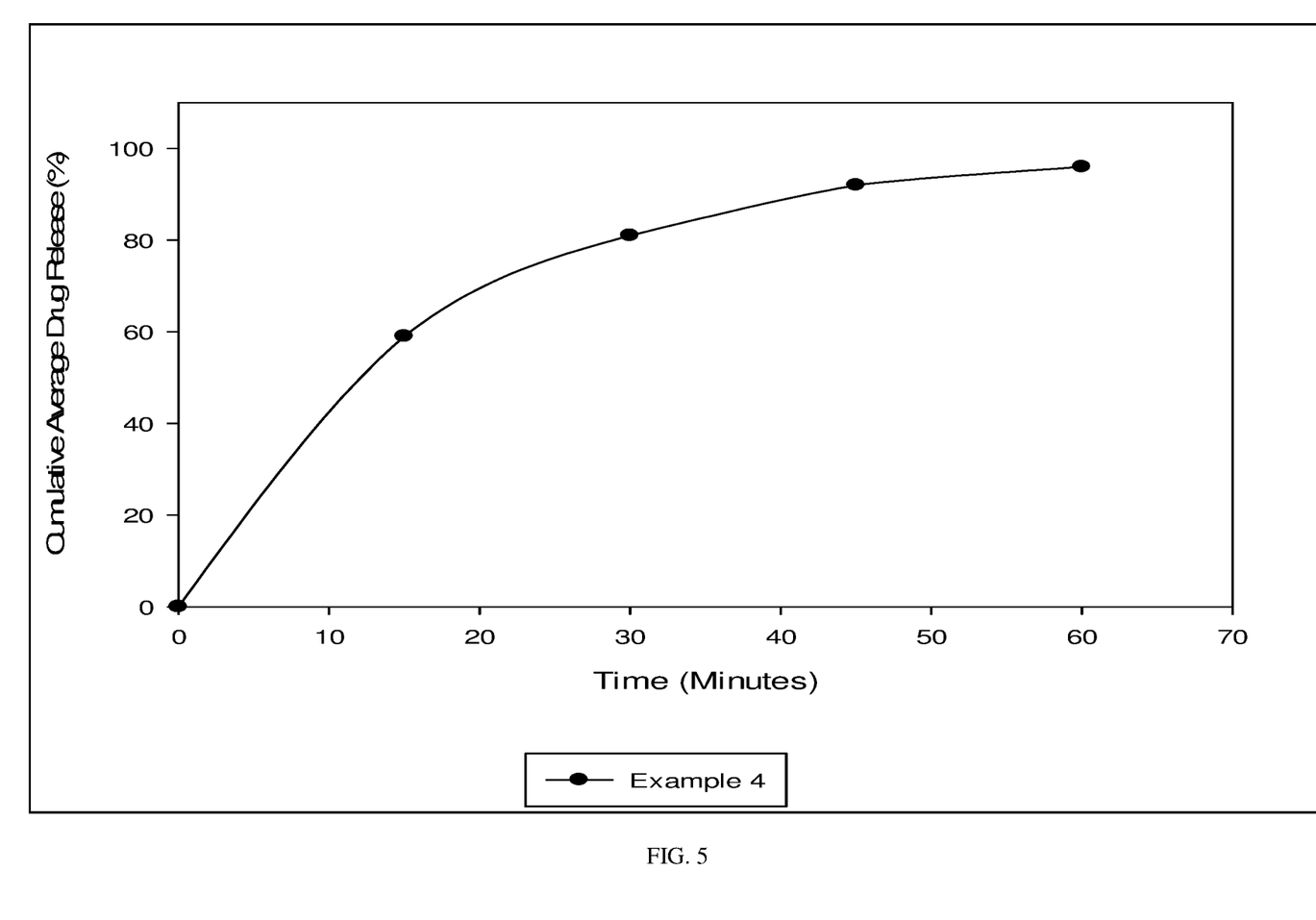
FIG. 5 is a chart showing the dissolution profile (% cumulative average drug released vs. time) of gummy dosage forms formed in accordance with Example 4.

FIG. 5 shows, with respect to gummies formed in accordance with Example 5, the plot of the dissolution profile (% cumulative average drug released vs. time) of gummy dosage forms formed in accordance with Example 4. Dissolution profile analysis was performed in water medium, using United States Pharmacopeia-apparatus II (Paddle Apparatus), five hundred milliliters (500 ml) water as medium, and at hundred rotations per minute (100 rpm).

Forced degradation or stress testing means purposeful degradation of active ingredient in a dosage form to predict the stability of a drug substance in a drug product with effects on purity, potency, and safety. It is imperative to know the impurity profile and behavior of a drug substance under various stress conditions associated with manufacturing process and associated stress conditions. The nature of the stress testing depends on the individual drug substance and the type of drug product (e.g., solid oral dosage, lyophilized powders, and liquid formulations).

Results of a forced degradation study performed at about ninety degrees Celsius (90° C.) for about eight hours the dosage forms formed in accordance with Example 3 are tabulated in Table 7.

TABLE 7

| | Time (hours) | | | | | |
|---|---|---|---|---|---|---|
| | 0 | 1 | 2 | 4 | 6 | 8 |
| Temperature (Celsius) | 92-95 | 92-95 | 92-95 | 92-95 | 92-95 | 92-95 |
| Solid Content (Brix) (% w/w) | 70 | 70 | 70 | 70 | 70 | 70 |
| Loss on Drying[1] (% w/w) | 20.87 | 19.82 | 19.32 | 20.35 | 20.33 | 22.25 |
| Assay (% w/w) | 96.4 | 100.1 | 104.9 | 101.8 | 102.3 | 96.4 |
| Individual Impurity (% w/w) | 0.19 | 0.14 | 0.36 | 0.32 | 0.3 | 0.36 |
| Total Impurity (% w/w) | 0.3 | 0.3 | 0.7 | 1 | 0.9 | 0.9 |

[1]Loss on drying performed by drying at a temperature in the range of about 95° C. to about 105° C. for 6-hours.

Results of a forced degradation study performed at about ninety degrees Celsius (90° C.) for about eight hours the dosage forms formed in accordance with Example 4 are tabulated in Table 8.

TABLE 8

| | Time (hours) | | | | | |
|---|---|---|---|---|---|---|
| | 0 | 1 | 2 | 4 | 6 | 8 |
| Temperature (Celsius) | 92-95 | 92-95 | 92-95 | 92-95 | 92-95 | 92-95 |
| Solid Content (Brix) (% w/w) | 73 | 73 | 73 | 73 | 73 | 73 |
| Loss on Drying[1] (% w/w) | 14.7 | 15.4 | 16.5 | 18 | 19.6 | 19.5 |
| Assay (% w/w) | 102.6 | 106.4 | 93.6 | 94.8 | 95.2 | 88.7 |
| Individual Impurity (% w/w) | 0.17 | 0.25 | 0.2 | 0.4 | 0.42 | 1.55 |
| Total Impurity (% w/w) | 0.25 | 0.41 | 0.39 | 0.67 | 0.83 | 2.30* |

[1]Loss on drying performed by drying at a temperature in the range of about 95° C. to about 105° C. for 6-hours.

Values for: total microbial count; combined yeast and mold count; and presence or absence of *e-coli, Staphylococcus aureus, Pseudomonas aeruginosa*, and *Salmonella* corresponding to the dosage forms formed in accordance with Examples 1, 3, and 4 are compiled in Table 9.

TABLE 9

| Test | EX 1 | EX 3 | EX 4 |
|---|---|---|---|
| Total Microbial Count (cfu/g) | <30 | <10 | <10 |
| Combined Yeast & Mold Count (cfu/g) | <10 | <10 | <10 |
| E-Coli | Absent | Absent | Absent |
| Staphylococcus aureus | Absent | Absent | Absent |
| Pseudomonas aeruginosa | Absent | Absent | Absent |
| Salmonella Species | Absent | Absent | Absent |

One preferred method of measuring the chewiness, hardness, compression energy, adhesion, cohesiveness, springiness, modulus, and gumminess (including any combination of any two or more of the foregoing) of gummy dosage forms of the present invention can be performed using a texture analyzers, such as those manufactured by Ametek, Inc., or similar such instruments. As will be discussed in greater detail below, texture analyzers can be set-up in a wide variety of ways. Additional details relating to the foregoing parameters and texture analyzers can be found in the Operating Instructions for the CT3 Texture Analyzer (Manual No. M08-372-F1116), which is incorporated herein by reference in its entirety. It should be understood that the present invention is not limited to parameters measured by a specific instrument and that other instruments may be used without departing from the spirit of the present invention.

Figure 2:
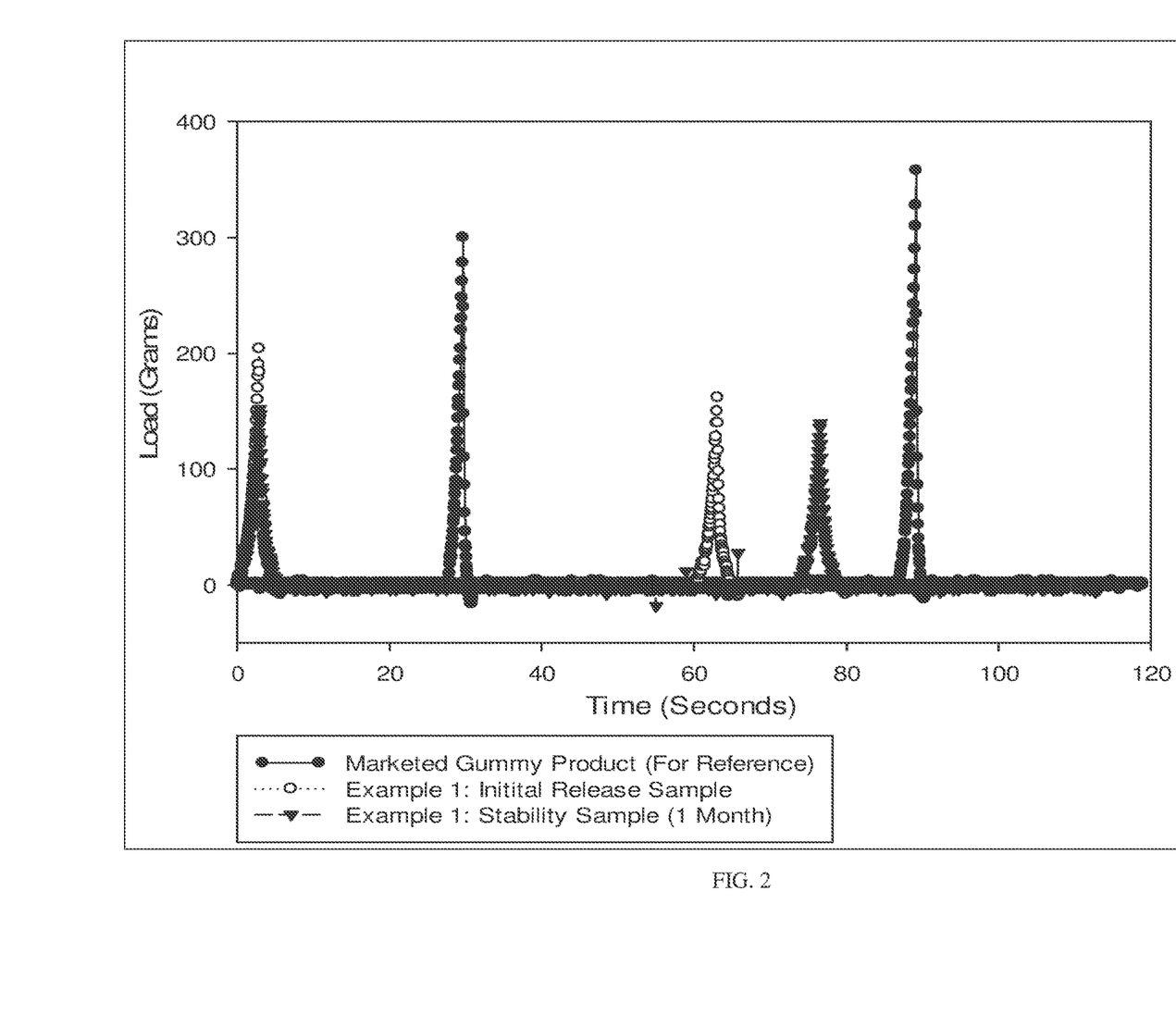
FIG. 2 is a chart showing the texture profiles (load in grams vs. time in seconds) for the marketed reference product and gummy dosage forms formed in accordance with Example 1 (initial release and stability sample)

FIG. 2 illustrates, with respect to gummies formed in accordance with Example 1, texture analysis load peaks registered approximately around three (3), thirty (30), sixty-three (63), seventy-five (75), and ninety (90) seconds for Marketed Product. The initial release and stability sample (kept for one-month at thirty degrees Celsius (30° C.) and seventy-five percent (75%) relative humidity (RH)) of Example 1, which was performed using TA9 probe and TA-STF fixture and ten thousand gram (10,000 g) load cell and two gram (2 g) trigger load, over six millimeters (6.0 mm) using two millimeter/second (2 mm/s) pretest speed and using a data rate of twenty points per second (20 points/second).

Figure 3:
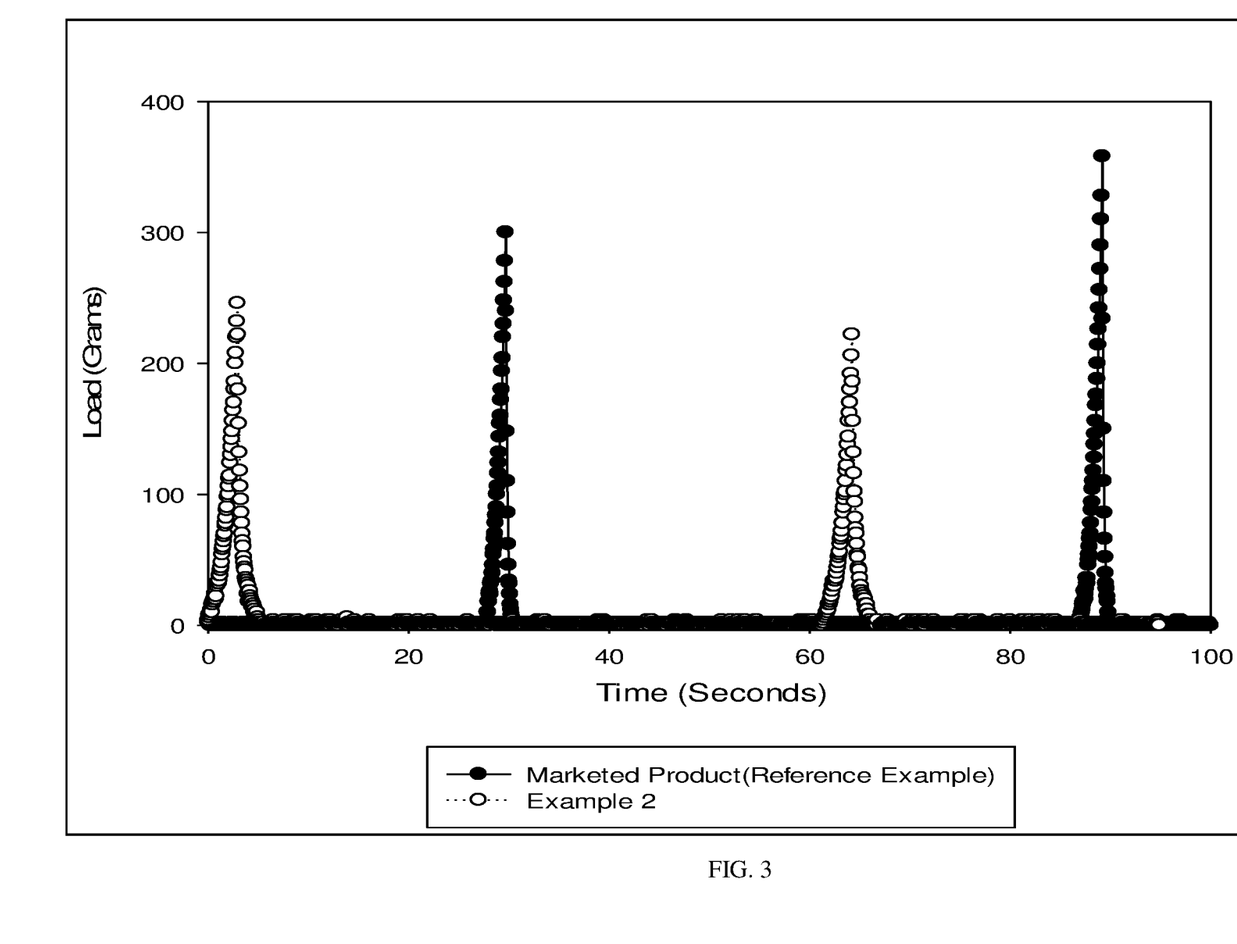
FIG. 3 is a chart showing the texture profiles (load in grams vs. time in seconds) for the marketed reference product and gummy dosage forms formed in accordance with Example 2.

FIG. 3 illustrates, with respect to gummies formed in accordance with Example 2, texture analysis load peaks registered at approximately around three (3), twenty-nine (29), sixty-five (65), and eighty-nine (89) seconds for Marketed Product, and example 2 which was performed using TA9 probe and TA-STF fixture and ten thousand-gram (10,000 g) load cell and two-gram (2 g) trigger load, over six millimeters (6.0 mm) using two millimeter/second (2 mm/s) pretest speed and using a data rate of twenty points per second (20 points/second).

Figure 4:
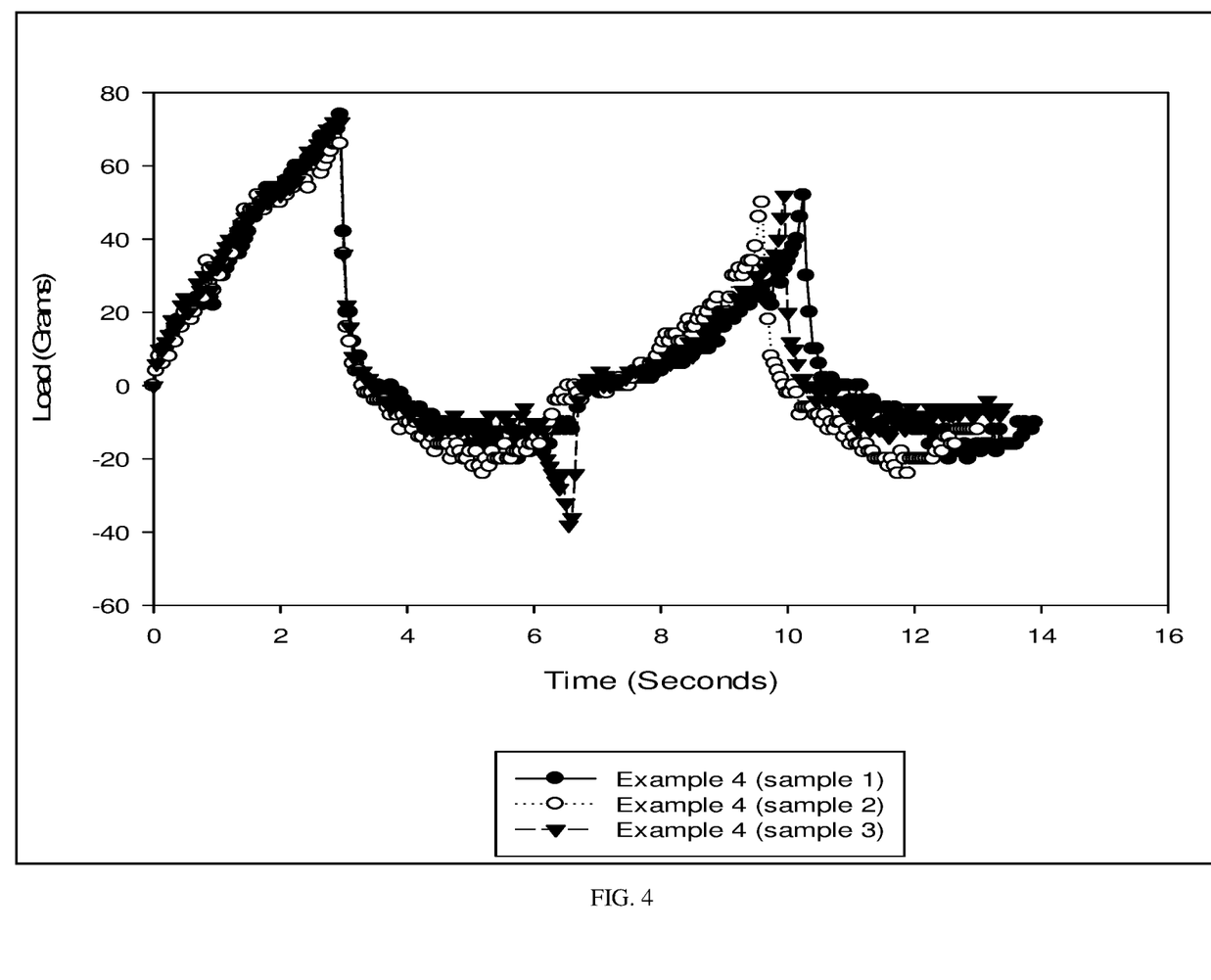
FIG. 4 is a chart showing the texture profiles (load in grams vs. time in seconds) for the marketed reference product and gummy dosage forms formed in accordance with Example 4.

FIG. 4 illustrates, with respect to gummies formed in accordance with Example 4, texture analysis load peaks registered at approximately around three (3), and ten (10) seconds and minimum load registered around seven (7) seconds for example 4 which was performed using TA9 probe and TA-STF fixture and twenty-five-thousand gram (25,000 g) load cell and five-gram (5 g) trigger load over six millimeters (6.0 mm) using two millimeter/second (2 mm/s) pretest speed and using a data rate of twenty points per second (20 points/second).

Texture characterization values, including values for average hardness (cycles 1 and 2, shown in grams), average adhesiveness (shown in millijoules), and average fracturability (shown in grams), corresponding to MGP 1, a second reference product (hereinafter referred to as "MGP 2"), and the dosage forms formed in accordance with Examples 1 and 2 are compiled in Table 10.

TABLE 10

| Sample | Average Hardness Cycle 1 | Average Adhesiveness | Average Fracturability (with 1% load) | Average Hardness Cycle 2 |
|---|---|---|---|---|
| MGP 1 | 225 | — | — | 227 |
| MGP 2 | 300 | 0.1 | 2 | 358 |
| EX 1 | 197 | 1 | 10 | 166 |
| EX 1[1] | 167 | 1 | 8 | 146 |
| EX 2 | 98 | 0.7 | 2 | 66 |

Footnote
[1]Example 1 (1 Month Stability) (30° C./75% RH).

Texture characterization values, including values for average cohesiveness, average springiness (shown in millimeters), average gumminess (shown in grams), and average chewiness (shown in millijoules), corresponding to MGP 1, MGP 2, and the dosage forms formed in accordance with Examples 1 and 2 are compiled in Table 11.

TABLE 11

| Sample | Average Cohesiveness | Average Springiness | Average Gumminess | Average Chewiness |
|---|---|---|---|---|
| MGP 1 | 1 | 15 | 167 | 27 |
| MGP 2 | 1 | 60 | 370 | 217 |
| EX 1 | 1 | 16 | 115 | 22 |
| EX 1[1] | 1 | 20 | 83 | 20 |
| EX 2 | 0.4 | 5 | 39 | 2 |

Footnote
[1]Example 1 (1 Month Stability) (30° C./75% RH).

Gummy dosage forms produced using carrageenan based gelling agents can be preferable because they exhibit exceptional freeze-thaw stability. Freeze-thaw stability refers to an ingredient's or a product's ability to remain stable (resist degradation, deterioration, etc.) when exposed to extreme temperature conditions, such as freezing or overheating. Freeze-thaw stability testing is often used to determine if an ingredient or a product can withstand (remain stable) when exposed to temperature fluctuations that may occur during transportation.

In certain embodiments of the present invention, the gummy (i.e., gummy) pharmaceutical dosage forms have a preferred recommended storage temperature ranging from about twenty degrees Celsius (20° C.) to about twenty-five degrees Celsius (25° C.). In certain embodiments of the present invention, the chewable/gummy pharmaceutical dosage forms exhibit a freeze-thaw stability providing minimal changes to the texture characterization of the dosage form.

An exemplary freeze-thaw stability study was conducted of a chewable/gummy dosage form manufactured in accordance with certain aspects of the present invention (a gelatin based dosage form containing eighty milligrams (80 mg) of acetaminophen). Samples were kept in a storage environment having a temperature of negative twenty degrees Celsius (−20° C.) for forty-eight (48) hours. The samples were then transferred to a storage environment having a temperature of forty degrees Celsius (40° C.) and a relative humidity of seventy-five percent (75% RH), where they were kept for a duration of forty-eight (48) hours. Various physical parameters of the samples were then tested. The results of the freeze-thaw stability test are summarized in Table 12.

TABLE 12

| Condition | Initially | 1st Cycle | 2nd Cycle | 3rd Cycle |
|---|---|---|---|---|
| Hardness (g) (cycle 1) | 360 | 393.6 | 408 | 517.2 |
| Adhesiveness (mJ) | 0.42 | 0.52 | 0.06 | 0.24 |
| Fracturability (g) (with 1% load) | 180.8 | 250.4 | 257.6 | 297.2 |
| Hardness (g) (cycle 2) | 304.4 | 314 | 338 | 422.4 |
| Cohesiveness | 0.73 | 0.88 | 0.84 | 0.8 |
| Springiness (mm) | 19.17 | 43.63 | 43.53 | 60.57 |
| Gumminess (g) | 263.4 | 347.8 | 338.4 | 411.4 |
| Chewiness (mJ) | 51.4 | 179.46 | 153.02 | 253.84 |

Transparent materials are materials that allow light to pass through them completely (for example distilled water). Translucent materials are materials that allow some, but not all, light to pass through them. Opaque materials are materials through which light cannot pass at all (e.g., conventional tablets or chewable tablet dosage forms are opaque).

In certain embodiments of the present invention, it is preferable for the gummy pharmaceutical dosage forms to be translucent.

It is generally accepted that opaque, transparent, or translucent visual appearance of a composition/formulation a physical property dependent on nature of ingredients of the composition. Visually opaque appearing compositions are composed of ingredients which are selective in their absorption of light frequencies; thus, they absorb only certain portions of the visible spectrum. The frequencies of the light spectrum which are not absorbed are reflected giving rise to color of such opaque compositions. Visually transparent compositions allow much of the light frequencies of the visible spectrum that falls on them to pass through. Liquids and aqueous solutions may be visually transparent. Absence of structural defects voids, cracks, etc. and unique molecular structure are mostly responsible for such visually transparent appearance.

Taking a cross section of gummy pharmaceutical dosage form, according to certain aspects of the present invention, by cutting it across its shortest axis based on its two dimensional shape into approximately ten (10) equidistant sections, preferably six (6) equidistant sections, more preferably two (2) equidistant sections and most preferably without cutting, yields a section of the gummy pharmaceutical dosage form of the present invention which has translucent appearance to visual appearance across the shortest axis.

Performance characterizations corresponding to the marketed product (L'IL CRITTERS GUMMY VITES®, hereinafter referred to as "MGP 1") and the dosage forms formed in accordance with Examples 1 and 2 are summarized in Table 13.

TABLE 13

| Sample | Appearance | Shape | Color | Taste |
|---|---|---|---|---|
| MGP 1 | Opaque | GBS[2] | Multiple Colors | Multiple Flavors |
| EX 1 | Translucent | GBS[2] | Red | Sharp/Crisp[3] |
| EX 1[1] | Translucent | GBS[2] | Red | Sharp/Crisp[3] |
| EX 1[2] | Translucent | GBS[2] | Red | Sharp/Crisp[3] |
| EX 2 | Translucent | GBS[2] | Red | Sharp/Crisp[3] |

Footnotes
[1]Example 1 (1 Month Stability) (30° C./75% RH).
[2]GBS is short form for Gummy Bear Shape.
[3]Taste being sharp and crisp relative to the marketed product.
4 - Example 1 (3 Month Stability) (25° C./60% RH).

A study was conducted to determine the palatability of gummy dosage forms manufactured in accordance with the present invention. In the study, participants consumed two variations of gummy dosage forms (Formulation-1 and Formulation-2) of the present invention. Formulation-1 is a gummy dosage form containing an eighty milligram (80 mg) dose of acetaminophen. Formulation-2 is a gummy dosage form containing a one hundred sixty milligram (160 mg) dose of acetaminophen. Participants were asked to rate the taste of the gummy dosage form on a 5-point scale ranging from: 1: very good; 2: good; 3: acceptable; 4: poor; and 5: bad. With respect to Formulation-1, nine (9) of ten (10) participants rated the taste of the gummy dosage form as being very good, and one (1) participant rated the taste of the gummy dosage form as being good. With respect to Formulation-2, eight (8) of ten (10) participants rated the taste of the gummy dosage form as being good, and two (2) participants rated the taste of the gummy dosage form as being very good.

Although specific advantages have been enumerated above, various examples may include some, none, or all of the enumerated advantages. Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Modifications, additions, and/or omissions may be made to the compositions, methods, and steps described herein without departing from the scope of the disclosure. For example, the ingredients of the composition and method for manufacture of the chewable pharmaceutical dosage forms may be integrated or separated. Moreover, the method for manufacture of the chewable pharmaceutical dosage forms and chewable pharmaceutical dosage forms disclosed herein may be prepared by more, fewer, or other ingredients and the methods described may include more, fewer, or other steps. Additionally, steps may be performed in any suitable order.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process for manufacture of a translucent chewable gel that is pharmaceutically suitable for oral administration comprising the steps of:
   (a) preparing a first mixture comprising water, a tonicity modifying agent, at least one taste enhancing agent, carrageenan, a buffering agent, a sugar, and a non-crystallizing polyol solution;
   (b) heating said first mixture to a temperature in the range of about 90° C. to about 105° C. to form a heated first mixture;
   (c) preparing a solution comprising water, a complexing agent, and acetaminophen;
   (d) combining said heated first mixture and said solution to form a combined mixture having a pH of at least 5;
   (e) maintaining a temperature of the combined mixture in the range of about 90° C. to about 105° C. until the combined mixture has a total solid content of at least about 70 brix to form a gummy mixture; and
   (f) transferring the gummy mixture to a forming device, allowing the gummy mixture to cool in the forming device to form said chewable gel, and removing the chewable gel from the forming device after a period of time of less than 30-minutes.

2. The process as claimed in claim 1, said sugar comprising a first sugar portion and a second sugar portion,
   step (a) including the steps of:
      combining and said water, said tonicity modifying agent, and said at least one taste enhancing agent to form mix-A;

combining said carrageenan, said buffering agent, and said first sugar portion to form mix-B;

combining said mix-A and mix-B to form mix-C; and adding said second sugar portion and said non-crystallizing polyol solution to mix-C to form said first mixture.

3. The process as claimed in claim 2, step (a) including the step of heating mix-A to a temperature in the range of about 50° C. to about 55° C. prior to forming said mix-C.

4. The process as claimed in claim 2, step (a) including the step of heating mix-C to a temperature in the range of about 90° C. to about 95° C. prior to adding said second sugar portion.

5. The process as claimed in claim 1, wherein said a tonicity modifying agent comprises sodium chloride.

6. The process as claimed in claim 1, wherein said at least one taste enhancing agent comprises neotame and corn syrup.

7. The process as claimed in claim 6, wherein said at least one taste enhancing agent further comprises bitter blocker powder and sucralose.

8. The process as claimed in claim 1, wherein said buffering agent comprises trisodium citrate.

9. The process as claimed in claim 1, wherein:

said sugar comprises sucrose, and said non-crystallizing polyol solution comprises maltitol solution.

\* \* \* \* \*